United States Patent [19]
Beattie et al.

[11] Patent Number: 5,874,306
[45] Date of Patent: Feb. 23, 1999

[54] CULTURING HUMAN PANCREATIC ENDOCRINE CELLS IN MEDIUM CONTAINING EXTRACELLULAR MATRIX FROM HUMAN BLADDER CARCINOMA CELLS

[75] Inventors: Gillian M. Beattie, Poway; Alberto Hayek, La Jolla, both of Calif.

[73] Assignee: The Regents of the University of California, Oakland, Calif.

[21] Appl. No.: 764,467

[22] Filed: Dec. 12, 1996

[51] Int. Cl.⁶ .............................. C12N 5/08; C12N 5/06; C12N 11/00
[52] U.S. Cl. .................. 435/366; 435/384; 435/387; 435/395; 435/404; 435/405; 435/406
[58] Field of Search ...................... 435/366, 384, 435/387, 391, 395, 404, 405, 406, 408

[56] References Cited

U.S. PATENT DOCUMENTS

| | | | |
|---|---|---|---|
| 5,315,000 | 5/1994 | Degen | 536/23.5 |
| 5,464,815 | 11/1995 | Chamow et al. | 514/8 |
| 5,510,263 | 4/1996 | Quaranta et al. | 435/240.243 |
| 5,532,341 | 7/1996 | Welte et al. | 530/351 |
| 5,571,509 | 11/1996 | Comoglio et al. | 424/94.5 |
| 5,587,309 | 12/1996 | Rubin et al. | 435/240.2 |

OTHER PUBLICATIONS

A. Hayek, et al., "Growth Factor/Matrix–Induced Proliferation of Human Adult β–Cells," *Diabetes* (Dec. 1995) 44: 1458–1460.

G.M. Beattie, et al., "Regulation of Proliferation and Differentiation of Human Fetal Pancreatic Islet Cells by Extracellular Matrix, Hepatocyte Growth Factor, and Cell–Cell Contact," *Diabetes* (Sep. 1996) 45: 1223–1228.

G.M. Beattie, et al., "Acid β–Galactosidase: A Developmentally Regulated Marker of Endocrine Cell Precursors n the Human Fetal Pancreas," *Journal of Clinical Endocrinology and Metabolism* (1994) 78(5): 1232–1240.

G.M. Beattie, et al., "Functional Impact of Attachment and Purification in the Short Term Culture of Human Pancreatic Islets," *Journal of Clinical Endocinology and Metabolism* (1991) 73(1): 93–98.

*Primary Examiner*—David M. Naff
*Attorney, Agent, or Firm*—Townsend and Townsend and Crew LLP

[57] ABSTRACT

Human pancreatic endocrine cells are proliferated without loss of hormone function in a culture medium containing extracellular matrix from bladder carcinoma cell lines in the substantial absence of hepatocyte growth factor/scatter factor. Proliferation is preferably carried out in the substantial absence of any peptide growth factors and nicotinamide. The cells may be proliferated in a monolayer on a solid substrate. Islets and islet-like cell clusters are proliferated without loss of insulin-secreting function by incubation in a medium containing extracellular matrix from a human bladder carcinoma cell line, preferably cell line ATCC HTB-9.

11 Claims, 7 Drawing Sheets

CULTURING HUMAN PANCREATIC ENDOCRINE CELLS IN MEDIUM CONTAINING EXTRACELLULAR MATRIX FROM HUMAN BLADDER CARCINOMA CELLS

BACKGROUND OF THE INVENTION

1. Field of the Invention

This invention lies in the field of the growth and functionality of pancreatic cells.

2. Description of the Prior Art

Type I (insulin-dependent) diabetes mellitus is a widespread disease, arising from an autoimmune disorder in which insulin-secreting beta-cells in the pancreas are destroyed. The loss of these cells impairs the body's ability to assimilate glucose from the blood, and the resulting high glucose levels can lead to blindness, kidney disease, nerve damage, and ultimately death. Insulin injections are commonly used to compensate for the lack of beta cells, but blood sugar levels can still fluctuate widely. Methods of lessening the fluctuations have included the use of small, frequent doses of insulin and the use of mechanical pumps that mimic the action of the pancreas, but these require continuous or periodic maintenance, and the results are often of limited success. An alternative is a pancreatic transplant, but this requires major surgery and the availability of donor pancreases is limited.

A more promising option is the transplantation of islets of Langerhans, using tissue derived from either cadavers or human fetuses. Islets of Langerhans are clusters of cells in the pancreas that include the insulin-secreting beta cells, and their transplantation entails considerably less risk than the transplantation of a pancreas. Sources for islet transplantation include adult pancreatic tissue, fetal pancreatic tissue and islet-like cell clusters (ICCs). Fetal tissue offers a greater content of islets in proportion to its mass, as well as a greater capacity for proliferation with its less mature cells. Islet-like cell clusters are heterogeneous cell populations that include epithelial cells that differentiate after transplantation to form various types of cells including mature islets.

Islet tissue that is available for transplantation is scarce, however, and islets must be banked and transported in order to obtain sufficient islets for a single recipient. One means of permitting the accumulation needed to obtain a sufficient number of islets is cryopreservation. Ex vivo or in vitro proliferation, or the growth of islet tissue in culture media, is another. Ex vivo or in vitro proliferation are also of use in generating sufficient islet tissue for clinical and laboratory research.

Successful ex vivo or in vitro proliferation occurs when the proliferated cells retain their functionality as sources of insulin. Regulation of the proliferation and differentiation of human fetal pancreatic islet cells is dependent on interactions between cell-cell and cell-matrix contacts and specific growth factors. Unfortunately, the nature of these interactions, and in particular the relative effects of matrix and growth factors on growth vs. differentiation, are not known. This prevents one from selecting matrices and growth factors, or combinations of the two, that will achieve proliferation while retaining cell functionality.

It is known, for example, that cell division among adult human $\beta$-cells is induced by a combination of extracellular matrix and hepatocyte growth factor/scatter factor (HGF/SF), the latter being one of a variety of peptide growth factors that have been tested. The cell proliferation that is achieved, however, is accompanied by a downregulation of islet-specific gene expression. Cell transplantation experiments performed with a cell suspension of proliferated cells failed to produce mature endocrine cells. The use of nicotinamide, a potent inducer of endocrine differentiation, in a suspension of the cells resulted in new islet formation, but this was accompanied by considerable cell attrition, which canceled much of the benefit of the new cell formation.

A method and growth medium are therefore sought that will result in the proliferation of islets and ICCs at a substantial rate with minimal or no loss of insulin secreting function.

SUMMARY OF THE INVENTION

It has now been discovered that when human pancreatic endocrine cells, including both islets and islet precursors, are proliferated in extracellular matrices derived from bladder carcinoma cell lines in the substantial absence of HGF/SF, the proliferated cells undergo substantially less of a loss of insulin generating and secreting function when compared to proliferation in the same extracellular matrices in the presence of HGF/SF. Particularly effective results are obtained with the human bladder carcinoma cell line HTB-9. The incubation is preferably performed in the substantial absence of any peptide growth factors, and most preferably also in the substantial absence of nicotinamide. These discoveries provide an effective means of expanding endocrine cell populations in culture before transplantation, thereby increasing the number of functioning transplants that can be made from cells derived from a single source or from a limited number of sources, and alternatively increasing the number of functional cells available for clinical and laboratory usage in general.

These and other advantages and features of the invention are more fully explained below.

BRIEF DESCRIPTION OF THE FIGURES

FIG. 1b is a bar graph comparing rates of insulin release from human fetal ICCs proliferated in three of the extracellular matrices of FIG. 1a.

FIG. 2c is a plot of insulin content vs. time, for the said human fetal ICCs as FIG. 2a.

FIG. 4b is a plot of insulin content vs. time, for the said human adult islets as FIG. 4a.

DETAILED DESCRIPTION OF THE INVENTION AND PREFERRED EMBODIMENTS

Figure 1A:
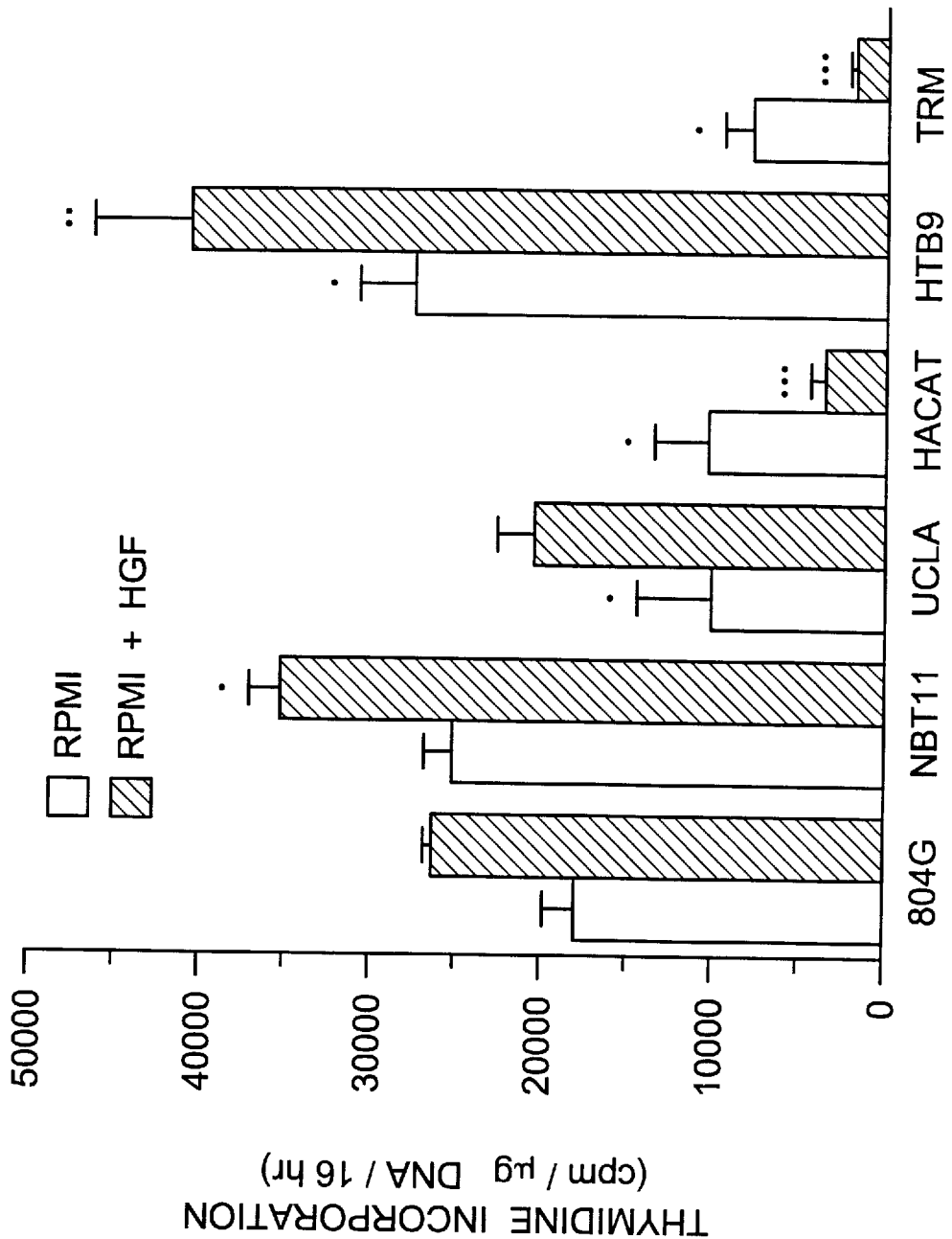
FIG. 1a is a bar graph comparing the degrees of proliferation of human fetal ICCs in six different extracellular matrices.

This invention addresses the proliferation of cells in culture, including both ex vivo and in vitro. While the terms are similar, their meaning is often distinguished in the art by using "ex vivo" to refer to cells drawn directly from a living organism, and "in vitro" to refer to cells grown in culture (regardless of the culture medium). In the context of this invention, this distinction would be that in vitro cells undergo growth in culture prior to being proliferated in accordance with this invention. The term "in culture proliferation" or "proliferation in culture" is used in this specification and in the claims attached hereto to encompass both, i.e., the proliferation of cells derived either ex vivo or in vitro prior to proliferation in accordance with this invention.

The term "extracellular matrix" is used herein to denote substances that are secreted by cells, and that serve as the scaffolding in tissue organization and migration, especially of embryonic cells during development. The extracellular matrices of bladder carcinoma cells are complexes of glycoproteins including fibronectin, laminin, heparan sulfate, and dermatan sulfate proteoglycans, and collagens, as well as certain growth factors including endothelial cell growth factor (ECGF), transforming growth factor β1 (TGF-β1), and under certain conditions HGF/SF. The matrix of HTB-9, however, does not contain HGF/SF, and this invention is directed to matrices from bladder carcinoma cells in general that do not contain significant quantities of HGF/SF.

The term "general absence" is used herein to indicate that any HGF/SF present in the culture medium is at a concentration low enough that any increase the proliferation rate of the cells due to the HGF/SF present does not exceed about 20%, and preferably does not exceed about 10%, both relative to the proliferation caused by the extracellular matrix alone or in combination with the other components of the culture medium. The term "substantial absence" is used herein to indicate that any HGF/SF present in the culture medium is at a concentration low enough that any effect that it has on the proliferation or functionality of the cells is either not detectable or within error limits by conventional methods of detection such as those used in the examples herein. Both terms include the total absence of HGF/SF. When one or both of these terms in used in connection with growth factors other than HGF/SF, the meaning is the same as that set forth above. When one or both of these terms is used in connection with nicotinamide, the meaning is analogous to that set forth above, i.e., the degree of cell differentiation due to the presence of nicotinamide is compared relative to the degree of cell differentiation due to the extracellular matrix alone or in combination with the other components of the cell culture.

Bladder carcinoma cells whose matrices are used in the present invention are preferably those from mammalian species, including livestock, household pets, and species used in laboratory experimentation, as well as humans. Human bladder carcinoma cells are preferred, and the most preferred is HTB-9.

The invention extends to pancreatic cells in general, including both ICCs and islets. The proliferation of these cells is performed in culture, preferably a liquid tissue culture medium, which includes any liquid solution that contains the appropriate solutes to preserve living cells and tissue. Many types of mammalian tissue culture media are known in the literature and available from commercial suppliers, such as Sigma Chemical Company, St. Louis, Mo., U.S.A.; Aldrich Chemical Company, Inc., Milwaukee, Wis., U.S.A.; and Gibco BRL Life Technologies, Inc., Grand Island, N.Y., U.S.A. Examples of media that are commercially available are Basal Medium Eagle, CRCM-30 Medium, CMRL Medium-1066, Dulbecco's Modified Eagle's Medium, Fischer's Medium, Glasgow Minimum Essential Medium, Ham's F-10 Medium, Ham's F-12 Medium, High Cell Density Medium, Iscove's Modified Dulbecco's Medium, Leibovitz's L-15 Medium, McCoy's 5A Medium (modified), Medium 199, Medium 199, Minimum Essential Medium Eagle, Alpha Minimum Essential Medium, Earle's Minimum Essential Medium, Medium NCTC 109, Medium NCTC 135, RPMI-1640 Medium, William's Medium E, Waymouth's MB 7521 Medium, and Waymouth's MB 705/1 Medium. Further media suitable for use in this invention are listed in Atlas, R. M., et al., *Handbook of Microbiological Media*, CRC Press, Boca, Raton, La. (1993), and in Freshney, *Culture of Animal Cells, A Manual of Basic Technique*, Third Edition, Wiley-Liss, New York (1994). As indicated above, media among those listed or referenced in this paragraph that are suitable for use in this invention are those in which HGF/SF is generally or substantially absent.

Techniques and methods for establishing a primary culture of cells for use in the in vitro and ex vivo methods of the invention are known to those of skill in the art. See for example Freshney (1994) and the references cited therein; Humason, *Animal Tissue Techniques, Fourth Edition*, W. H. Freeman and Company (1979), and Ricciardelli et al., *In Vitro Cell Dev. Biol.* 25: 1016–1024 (1989).

Islets (the term is used herein to include both adult islets and ICCs) can be isolated from pancreas tissue by methods known to those skilled in the art. Cell growth can be performed with free-floating cells suspended in culture media, or in monolayers of the cells, preferably on a culture-coated inert solid substrate such as a microscope slide. The monolayers are formed by methods known in the art.

Incubation is generally performed under conditions known to be optimal for cell growth. Such conditions may include for example a temperature of approximately 37° C. and a humidified atmosphere containing approximately 5% $CO_2$. The duration of the incubation can vary widely, depending on the desired results. In general, incubation is preferably continued until the cells begin to lose enough of their insulin secretion functionality to impose significant limits on their usefulness. As an approximate rule, the loss of over 25% of the rate of insulin secretion relative to fresh cells may be considered a limit. The degree of growth is conveniently expressed as an increase in the DNA content of the cell population, and a preferred degree of growth is an approximately three-fold or more increase in DNA content. Expressed as a range, a preferred degree of growth is an increase in DNA content from about three-fold to about twelve-fold.

Techniques well known in the art can be used for DNA content, including Southern blotting, Northern blotting, PCR analysis, and uptake of radioactive or fluorescent nucleotides. Literature sources for Southern and Northern blotting techniques include Berger and Kimmel, *Guide to Molecular Cloning Techniques, Methods in Enzymology*, Vol. 152, Academic Press, Inc., San Diego, Calif.; Sambrook et al. (1989) *Molecular Cloning—A Laboratory Manual* (2nd ed.), Vol. 1–3, Cold Spring Harbor Laboratory, Cold Spring Harbor Press, New York,; and *Current Protocols in Molecular Biology*, F. M. Ausubel et al., eds., Current Protocols, a joint venture between Greene Publishing Associates, Inc. and John Wiley & Sons, Inc., (1994 Supplement). Useful information is also found in product information from manufacturers of biological reagents and experimental equipment. Such manufacturers include the SIGMA Chemical Company (St. Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), and Applied Biosystems (Foster City, Calif.). For PCR analysis, examples including the polymerase chain reaction (PCR), the ligase chain reaction (LCR), Qβ-replicase amplification and other RNA polymerase mediated techniques (e.g., NASBA) are found in Berger et al., Sambrook et al., and Ausubel et al., as well as Mullis et al. U.S. Pat. No. 4,683,202 (1987); *PCR Protocols A Guide to Methods and Applications*, Innis et al., eds., Academic Press Inc., San Diego, Calif. (1990); Arnheim et al. (Oct. 1, 1990) C&EN 36–47; *The Journal Of NIH Research*, Vol. 3, 81–94 (1991); Kwoh et al., *Proc. Natl. Acad. Sci. USA*, Vol. 86, 1173 (1989); Guatelli et al., *Proc. Natl. Acad. Sci. USA*, Vol. 87, 1874 (1990); Lomell et al., *J. Clin. Chem.*, Vol. 35: 1826 (1989); Landegren et al., *Science*, Vol. 241: 1077–1080 (1988); Van Brunt, *Biotechnology*, Vol. 8: 291–294 (1990); Wu and Wallace, *Gene*, Vol. 4: 560 (1989); Barringer et al., *Gene*, Vol. 89: 117 (1990); and Sooknanan and Malek, *Biotechnology*, Vol. 13: 563–564 (1995). Improved methods of cloning in vitro amplified nucleic acids are described in Wallace et al., U.S. Pat. No. 5,426,039.

The following examples are offered for purposes of illustration, and are intended neither to limit nor to define the invention in any manner. All literature citations throughout this specification, including those cited above as well as those in the following examples, are hereby incorporated herein by reference.

EXAMPLES

Human fetal pancreatic tissue used in the following experiments was provided by the Anatomic Gift Foundation (Laurel, Md., U.S.A.) and Advanced Bioscience Resources (Oakland, Calif., U.S.A.). Tissue was processed by according to standard procedures and the ICCs that were formed were cultured for three days in the presence of HGF/SF. Human adult islets were provided by the Diabetes Research Institute (Miami, Fla., U.S.A.) and the Islet Isolation Core Facility (St. Louis, Mo., U.S.A.). The adult islets were isolated by an automated method and further purified by hand picking single islets, 50–150 microns in diameter after dithizone staining, selected by their translucent appearance.

Extracellular matrices were derived from the following cell lines:

rat bladder carcinoma cell line 804G—provided by Dr. V. Quaranta, La Jolla, Calif. U.S.A.

rat bladder carcinoma cell line NBT-11—obtained from ATCC, Rockville, Md., U.S.A., ATCC No. CRL-1655 human bladder carcinoma cell line HTB-9—obtained from ATCC, Rockville, Md., U.S.A., ATCC No. HTB-9 human squamous carcinoma cell line SCC-25—obtained from ATCC, Rockville, Md., U.S.A., ATCC No. CRL-1628 human keratinocyte cell line HaCaT—provided by Dr. D. Salomon, La Jolla, Calif., U.S.A.

human lung carcinoma UCLA—provided by Dr. R. Reisfeld, La Jolla, Calif., U.S.A.

human fetal pancreatic tumor line TRM-1—derived from human fetal pancreatic tissue by the inventors herein Extracellular matrices were derived from monolayers of the above cell lines, the monolayers having been prepared by standard procedures. See for example Beattie, G. M., et al., *J. Clin. Endocr. Metab.* 73: 93–98 (1991), and Gospodarowicz, D., *Cell Culture Methods for Molecular and Cell Biology*, D. W. Barnes et al., eds., pp. 275–295, Alan R. Liss, Inc., New York, N.Y. (1984).

For the proliferation tests, fifty ICCs or adult islets were plated per well, and four replicate wells were used for each determination.

For tests in which DNA synthesis and insulin content and secretion were measured, monolayers of the ICCs or islets were pulsed with 1.0 Ci/mL of [methyl-$^3$H] thymidine (specific activity 25 Ci/mmol, Amersham, Arlington, Ill., U.S.A.) in newly replenished medium. After 16 hours, medium was collected to determine insulin secretion while thymidine incorporation into DNA and insulin extractable from cells were quantified. For the standard methods used, see Beattie et al. (1991) and Otonkoski, T., et al. *J. Clin. Invest.* 92: 1459–1466 (1993). Acute insulin release following stimulation with glucose was assayed in static incubations, again by standard procedures; see Beattie et al. (1991). See for example Beattie, G. M., et al., *J. Clin. Endocr. Metab.* 73: 93–98 (1991). Insulin was measured with a solid phase radioimmunoassay, while DNA content was measured fluorometrically. See for example Hinegardner, R. T., *Anal. Biochem.* 39: 197–201 (1971). Incorporation of [$^3$H] thymidine was determined by liquid scintillation counting of trichloroacetic acid precipitates of the sonicated cells.

For statistical analyses, experiments were carried out on at least three different preparations of ICCs or islets. The statistical significance of observed differences was analyzed by ANOVA and Fischer's protected least significant difference test with 95% level as the limit of significance.

EXAMPLE 1

This example illustrates the proliferation of human fetal ICCs in extracellular matrices from each of the six cell lines in a culture medium consisting of RPMI-1640, both with and without the additional presence of 10 ng/mL of HGF/SF, and insulin production from the proliferated ICCs in the three bladder carcinoma cell lines.

The ICC monolayers were plated on the matrices, and after five days of culture, proliferation was measured by assaying the monolayers for [$^3$H]-thymidine incorporation. The proliferation results are shown in FIG. 1a, which is a bar graph showing comparative levels of thymidine incorporation, the open bars representing ICCs cultured in the matrices without HGF/SF present, and the shaded bars representing ICCs cultured in the matrices in the presence of HGF/SF. The error limits are also shown, and the single asterisk (*) denotes a statistical p value of <0.05, two asterisks () denote a statistical p value of <0.01, and three asterisks (*) denote a statistical p value of <0.001. These notations are used in all examples in this specification.

The data in FIG. 1a shows that the level of thymidine incorporation and hence the degree of proliferation were highest in the culture media containing extracellular matrices from the three bladder carcinoma cell lines, both with and without HGF/SF, with HTB-9 producing the highest results.

Figure 1B:
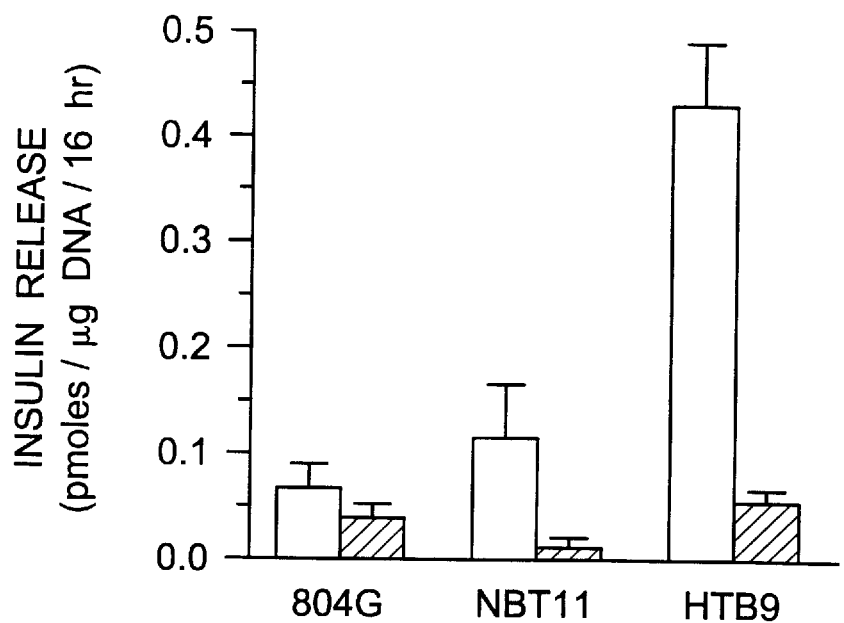
Figure 1C:
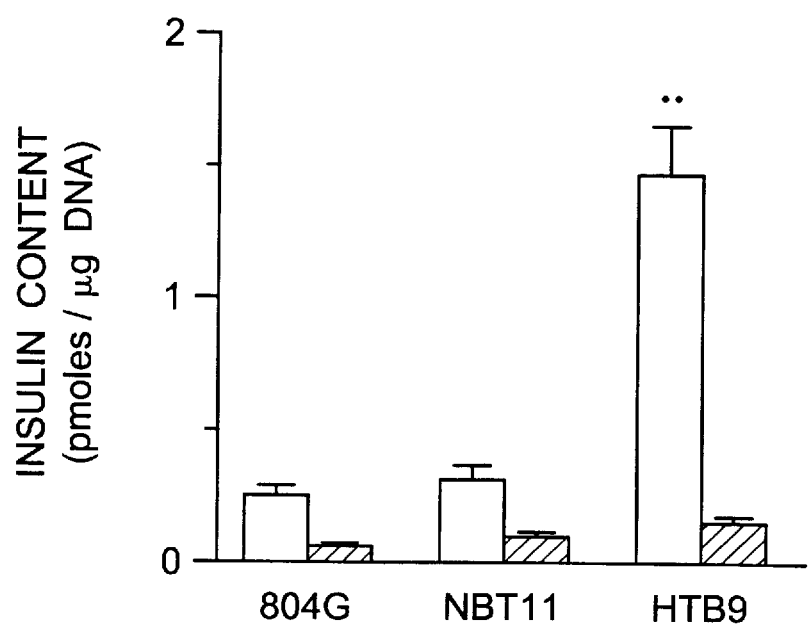
FIG. 1c is a bar graph comparing the insulin contents of the same human fetal ICCs as FIG. 1b.

The amounts of insulin secreted into the culture medium over a period of sixteen hours and the amounts of insulin extractable from the cells are shown in FIGS. 1b and 1c, respectively. Both sets of data were taken after five days of culture, as was the proliferation data of FIG. 1a. The open and shaded bars and asterisk markings have the same meaning in FIGS. 1b and 1c as in FIG. 1a. Comparisons between the open bars and the shaded bars in FIGS. 1b and 1c indicate that both the insulin release rate and content in the cells are significantly decreased in monolayers growing for five days in these matrices when HGF/SF is present, relative to those growing for five days in these matrices with no HGF/SF present. In the absence of HGF/SF, both the insulin content and release are significantly higher in cells grown on HTB-9 than on the other two bladder carcinoma cell lines.

EXAMPLE 2

The example focuses on the use of the extracellular matrix of HTB-9 with human fetal ICCs, and illustrates the time course of the growth of the ICCs in the presence or absence of HGF/SF, as well as the time course of insulin production (both release and cell content).

Figure 2A:
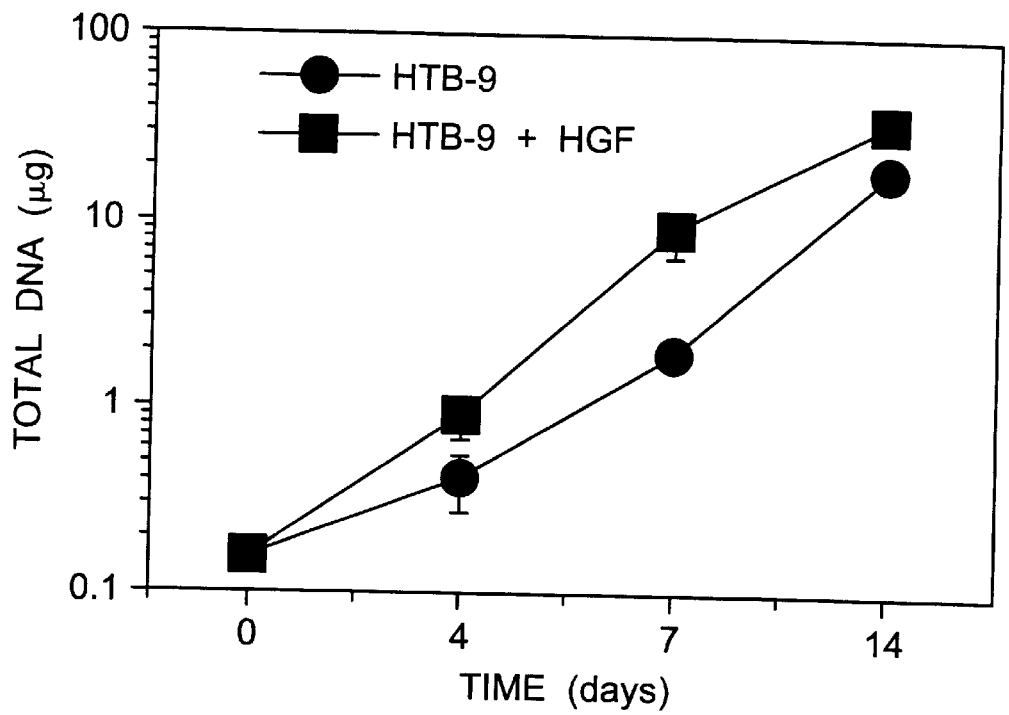
FIG. 2a is a plot of cell proliferation vs. time for human fetal ICCs incubated in HTB-9 extracellular matrix, with and without the added presence of HGF/SF.
Figure 2B:
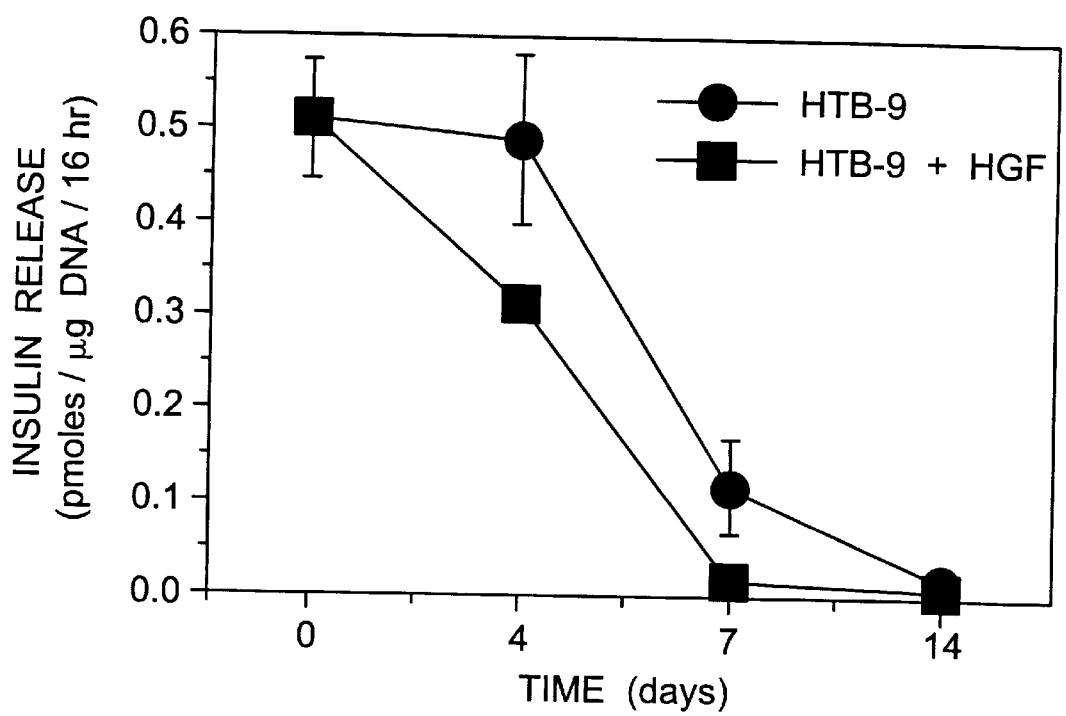
FIG. 2b is a plot of insulin release vs. time
Figure 2C:
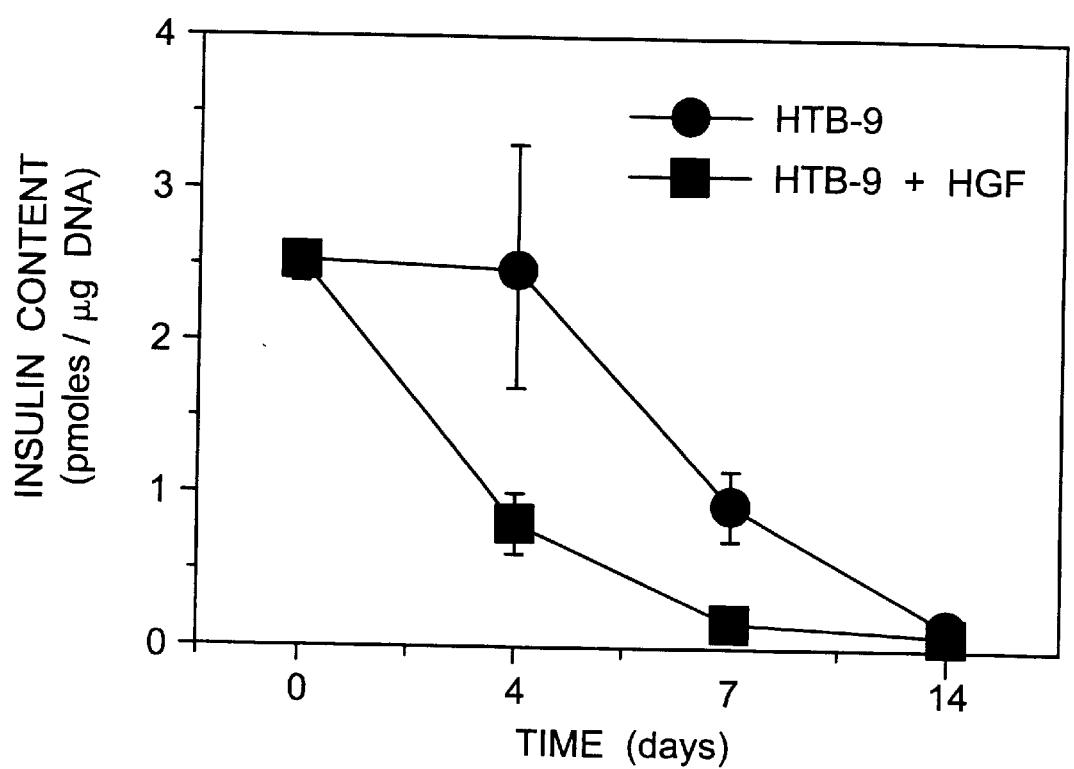

Using the same procedure as Example 1, the monolayers were assayed for total DNA, insulin release and insulin content at the start of the incubation, and then again at 4 days, 7 days and 14 days. The ICC growth data is shown in FIG. 2a, where the circles represent the tests performed on HTB-9 matrix without HGF/SF, and the squares represent the tests performed on HTB-9 matrix with HGF/SF. The plot shows that after 14 days the DNA content had increased by more than 100 times in the absence of HGF/SF and by more than 200 times in the presence of HGF/SF. The insulin release and cell content data are plotted in FIGS. 2b and 2c, respectively, where the circles and squares represent the same two media as in FIG. 2a. FIGS. 2b and 2c show that in the presence of HGF/SF, insulin release and content diminished rapidly, the release diminishing by 38% after four days and dropping to a barely detectable level after 14 days. Insulin content decreased even further, showing a 68% reduction after 4 days and likewise dropping to a barely detectable level after 14 days. In contrast, when monolayers were grown in the absence of HGF/SF, the insulin release and content did not drop significantly (as shown in the figures) and remained at the same level observed in ICCs that were free floating in petri dishes (data not shown) for the first four days. The differences in insulin levels observed at four days in the presence and absence of HGF/SF were significant ($p < 0.05$ for insulin release and $p < 0.001$ for insulin content). By the seventh day the differences were still significant ($p < 0.05$ for content).

EXAMPLE 3

This example confirms that the proliferative effect of HTB-9 matrix is not due to any presence of HGF/SF in the matrix, thus indicating that the matrix does not in fact contain HGF/SF.

Figure 3:
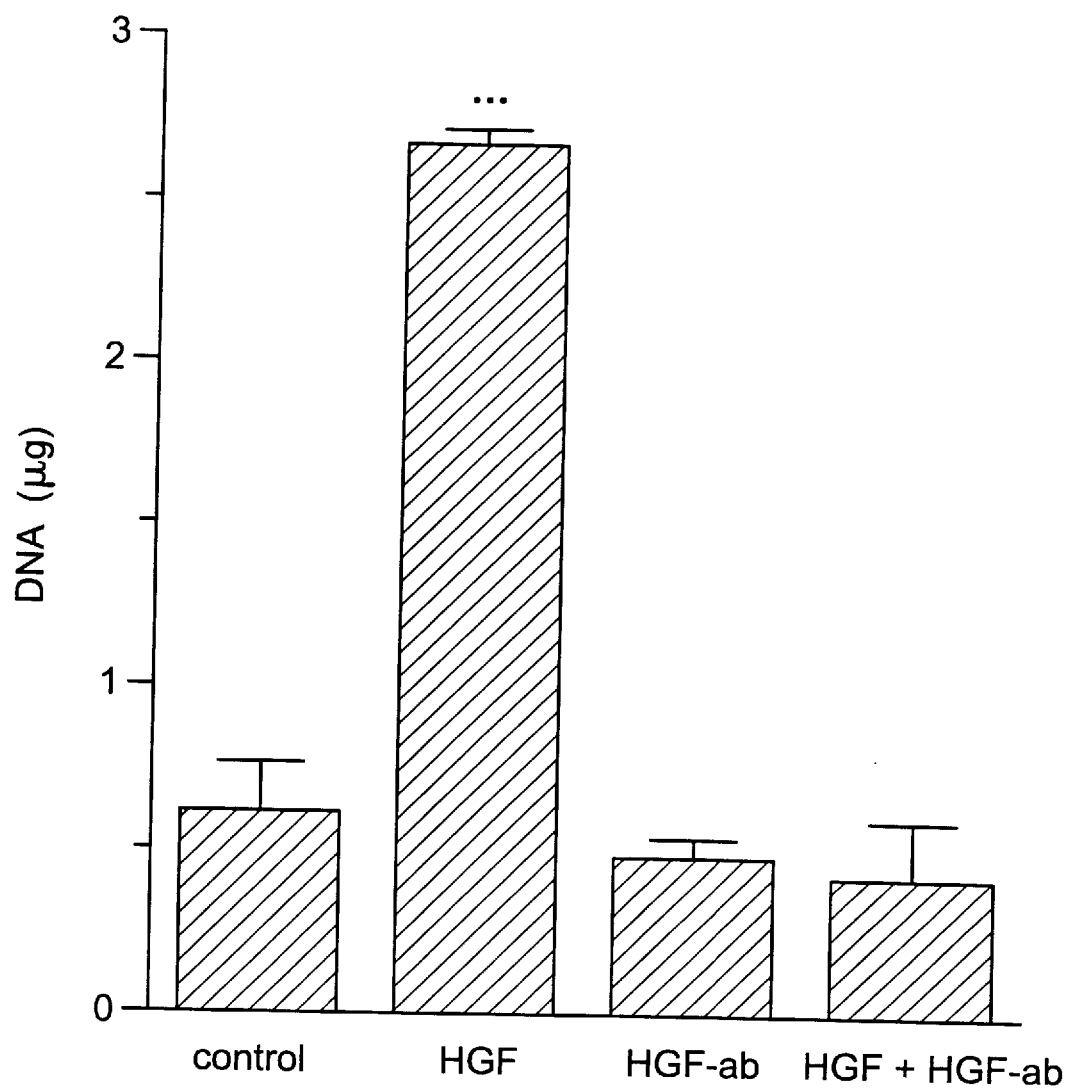
FIG. 3 is a bar graph comparing degrees of proliferation of human fetal ICCs in different media to determine whether there is any HGF/SF present.

Rabbit polyclonal antiserum specific for HGF/SF was added to the HTB-9 matrix at a 200-fold dilution, and human fetal ICC monolayers were proliferated on the matrix as in the preceding examples. The experiment included monolayers cultured in HTB-9 alone (as a control), HTB-9 plus HGF/SF at 10 ng/mL, HTB-9 plus the anti-HGF/SF antiserum, and HTB-9 plus both the HGF/SF at 10 ng/mL and the anti-HGF/SF antiserum. The total DNA contents were compared after one week of culture, and the results are presented in bar-graph form in FIG. 3. Comparisons between the bar heights indicate that the proliferative effect of HTB-9 matrix (without added HGF/SF, i.e., the control) is not due to HGF/SF storage in the matrix, since the first, third and fourth bars are of approximately equal height.

EXAMPLE 4

This example illustrates the proliferation of human adult islets in the extracellular matrix of HTB-9, both with and without HGF/SF, as well as the insulin content of the islets, both over a fourteen-day time period.

Figure 4A:
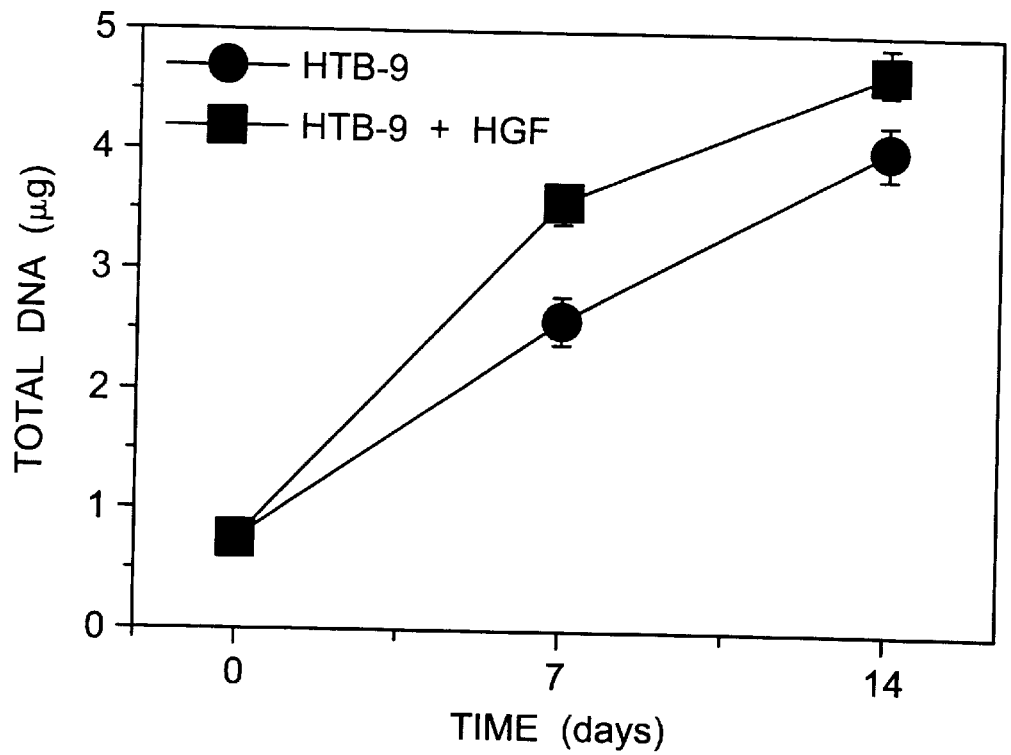
FIG. 4a is a plot of cell proliferation vs. time for human adult islets incubated in HTB-9 extracellular matrix, with and without the added presence of HGF/SF.
Figure 4B:
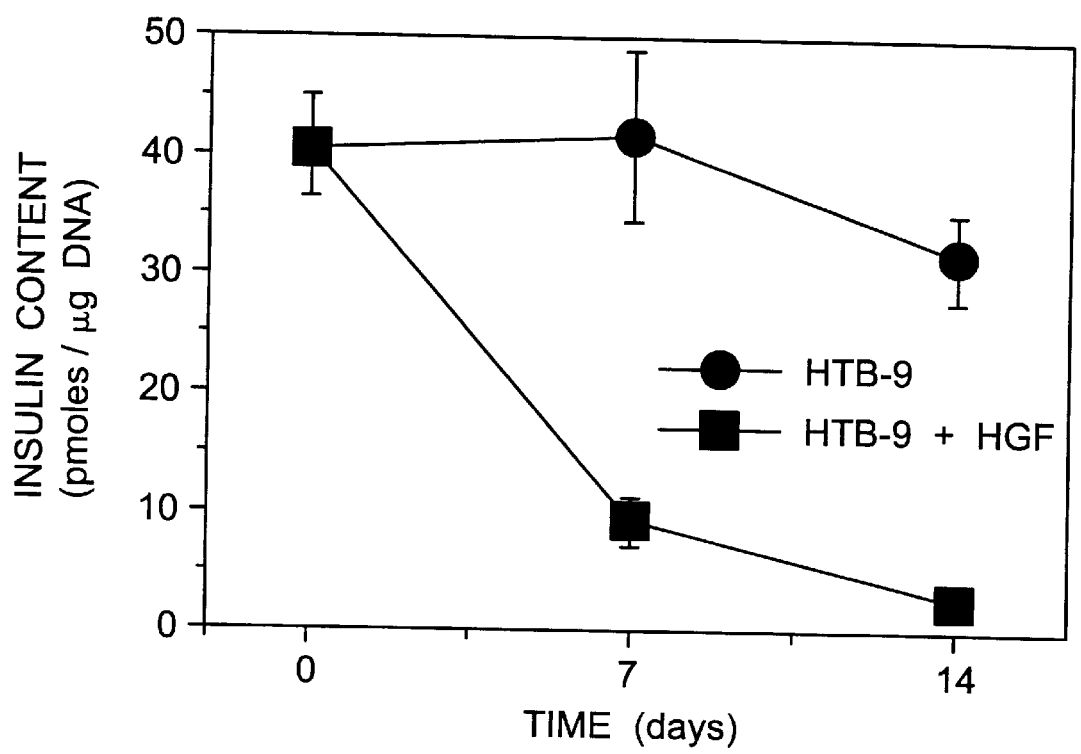

The amount of HGF/SF when present in these experiments was 25 ng/mL. The proliferation results are shown in FIG. 4a, and the insulin content results are shown in FIG. 4b. In both figures, the circles represent the tests performed on HTB-9 matrix without HGF/SF, and the squares represent the tests performed on HTB-9 matrix with HGF/SF.

The proliferation results show a three-fold increase in adult islet DNA after one week in monolayer, and a five-fold increase after two weeks, when using HTB-9 matrix alone. The addition of HGF/SF enhanced the proliferative effect of the matrix to four-fold and six-fold after one and two weeks, respectively. The increase in DNA was accompanied by a concomitant increase in cell number and [$^3$H]-thymidine incorporation (data not shown). By comparison, control islets kept floating in petri dishes or plated on tissue-coated dishes alone showed no increase in DNA content (data not shown).

The insulin content tests show a large drop in insulin content after one week in monolayer when using HTB-9 matrix in combination with HGF/SF, and no drop at all after the same time period when using HTB-9 alone. After two weeks, the insulin content in the presence of HTB-9 and HGF/SF dropped to a barely detectable level, while the insulin content with HTB-9 alone had dropped only slightly.

EXAMPLE 5

This example illustrates insulin release upon glucose stimulation, using human adult islets grown in the extracellular matrix of HTB-9, both with and without HGF/SF.

Figure 5A:
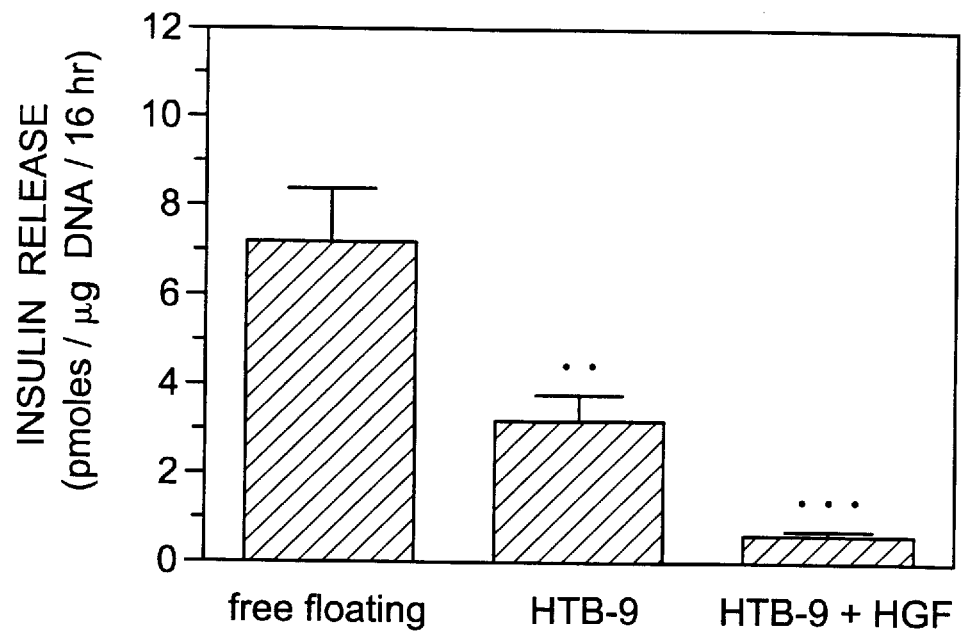
FIG. 5a is a plot of insulin release from human adult islets incubated in HTB-9 extracellular matrix, with and without the added presence of HGF/SF, upon a low level of glucose stimulation.

After five days in culture, the islet monolayers were stimulated overnight in glucose at 5.5 mM. Insulin release was determined and compared to insulin release from free-floating islets in petri dishes. The results are shown in the bar graph of FIG. 5a, which indicates that the insulin release was reduced in both cases relative to the free-floating islets. The reduction was much greater in the monolayers that had been proliferated in the medium containing HGF/SF.

Figure 5B:
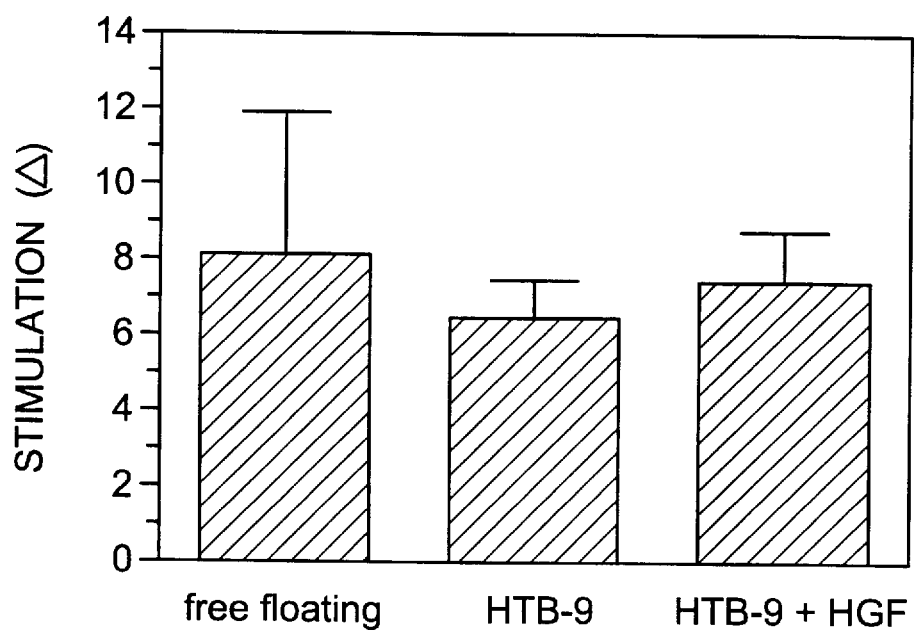
FIG. 5b is a similar plot taken upon a higher level of glucose stimulation.

The experiment was repeated but with acute stimulation at a glucose concentration of 16.7 mM. The results are shown in the bar graph of FIG. 5b. These results show that the ability of the islets to respond to acute glucose stimulation was unimpaired.

The foregoing is offered primarily for purposes of illustration. It will be readily apparent to those skilled in the art that the operating conditions, materials, procedural steps and other parameters of the invention described herein may be further modified or substituted in various ways without departing from the spirit and scope of the invention.

We claim:

1. A method for the proliferation in culture of human pancreatic endocrine cells, comprising incubating said cells in a culture medium containing extracellular matrix derived from a human bladder carcinoma cell line for a period of time sufficient to cause substantial proliferation without substantial loss of hormone function of said cells, said culture medium and extracellular matrix being essentially free of peptide growth factors, nicotinamide and hepatocyte growth factor/scatter factor.

2. A method in accordance with claim 1 in which said human bladder carcinoma cell line is human bladder carcinoma cell line ATCC No. HTB9.

3. A method in accordance with claim 1 comprising incubating said cells in said culture for a sufficient period of time to achieve at least an approximately 3-fold increase in DNA content.

4. A method in accordance with claim 1 comprising incubating said cells in said culture for a sufficient period of time to achieve an increase in DNA content ranging from about 3-fold to about 12-fold.

5. A method in accordance with claim 1 in which said human pancreatic endocrine cells are islet-like cell clusters.

6. A method in accordance with claim 1 in which said human pancreatic endocrine cells are adult islets.

7. A method in accordance with claim 1 comprising incubating a monolayer of said cells in said culture on a solid substrate.

8. A composition of matter comprising a cell culture medium containing human pancreatic endocrine cells in extracellular matrix derived from a human bladder carcinoma cell line, said culture medium and extracellular matrix being essentially free of peptide growth factors, nicotinamide and hepatocyte growth factor/scatter factor.

9. A composition of matter in accordance with claim 8 in which said human bladder carcinoma cell line is human bladder carcinoma cell line ATCC No. HTB-9.

10. A composition of matter in accordance with claim 8 in which said human pancreatic endocrine cells are islet-like cell clusters.

11. A composition of matter in accordance with claim 8 in which said human pancreatic endocrine cells are adult islets.

* * * * *